United States Patent
El Kadib et al.

(10) Patent No.: US 8,338,324 B2
(45) Date of Patent: Dec. 25, 2012

(54) ACTIVATING SUPPORTS BASED ON PHOSPHONIUM COMPLEXES

(75) Inventors: Abdelkrim El Kadib, Montpellier (FR);
Karine Molvinger, Montpellier (FR);
Daniel Brunel, Montpellier (FR);
Floran Prades, Nivelles (BE); Sabine Sirol, Wanthier-Brame (BE)

(73) Assignees: Total Petrochemicals Research Feluy, Seneffe (Feluy) (BE); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/747,834

(22) PCT Filed: Dec. 11, 2008

(86) PCT No.: PCT/EP2008/010521
§ 371 (c)(1),
(2), (4) Date: Apr. 13, 2011

(87) PCT Pub. No.: WO2009/074316
PCT Pub. Date: Jun. 18, 2009

(65) Prior Publication Data
US 2011/0184133 A1    Jul. 28, 2011

(30) Foreign Application Priority Data
Dec. 11, 2007   (EP) .................................. 07291495

(51) Int. Cl.
*C08F 4/02*      (2006.01)
*C08F 4/42*      (2006.01)
*C08F 4/6592*    (2006.01)

(52) U.S. Cl. ........ 502/120; 502/103; 502/121; 502/128; 502/152; 502/202; 526/129; 526/130; 526/133; 526/134; 526/145; 526/160; 526/943

(58) Field of Classification Search .................. 502/120, 502/132, 152, 202; 526/103, 120, 128, 132, 526/152
See application file for complete search history.

(56) References Cited

U.S. PATENT DOCUMENTS

| 5,587,439 | A | 12/1996 | Dimaio |
| 5,643,847 | A * | 7/1997 | Walzer, Jr. .................... 502/117 |
| 2002/0103072 | A1 | 8/2002 | Patrick et al. |
| 2002/0119890 | A1 | 8/2002 | Wenzel et al. |
| 2004/0162403 | A1 | 8/2004 | Shimizu et al. |
| 2005/0154167 | A1 | 7/2005 | Szul et al. |
| 2006/0235171 | A1 | 10/2006 | Lee et al. |
| 2006/0264320 | A1 | 11/2006 | Rodriguez et al. |
| 2006/0293474 | A1 | 12/2006 | Brant et al. |
| 2007/0117941 | A1 | 5/2007 | Brant |
| 2007/0276105 | A1 | 11/2007 | Razavi |

FOREIGN PATENT DOCUMENTS

| WO | 0153356 A | 7/2001 |
| WO | WO 02/26842 | 4/2002 |
| WO | 02038637 A | 5/2002 |
| WO | 2004026921 A | 4/2004 |
| WO | 2006065809 A | 6/2006 |
| WO | 2006080817 A | 8/2006 |
| WO | WO 2007/061526 | 5/2007 |

* cited by examiner

Primary Examiner — Caixia Lu

(57) ABSTRACT

The present invention relates to the covalent anchorage of non-coordinating anions on mineral supports to prepare activating supports for the polymerisation of ethylene and alpha-olefins and wherein the activating species is provided by a phosphonium-borate or phosphonium alane pair. The invention also discloses the concomitant covalent anchorage of zwitterionic systems containing both the non-coordinating anion and the counter cation parts of the activating supports.

11 Claims, No Drawings

ACTIVATING SUPPORTS BASED ON PHOSPHONIUM COMPLEXES

CROSS-REFERENCE TO RELATED APPLICATIONS

This application claims the benefit of PCT/EP2008/010521, filed Dec. 11, 2008, which claims priority from EP 07291495.5, filed Dec. 11, 2007.

The present invention discloses the preparation of solid activating systems for the polymerisation of olefins. Particularly, the present invention relates to an activating support for immobilising metallocene or post-metallocene complexes, in order to promote heterogeneous polymerisation of ethylene and alpha-olefins.

The polymerisation of olefins in the presence of single site complexes has mostly been described in homogeneous catalysis. In that type of polymerisation, the catalyst, the olefin monomer and the resulting polymer are all present in the same liquid phase, typically a solvent.

These catalysts are however not adapted to heterogeneous polymerisation, such as suspension or gas phase polymerisation. These processes offer many advantages, among others, they allow the preparation of a polymer in granular form having a defined particles size distribution.

It is known in the art of homogeneous olefin polymerisation catalysis to use metallocene complexes or α-diimine or 2,6-bis(imino)pyridyl complexes of late transition metal in combination with a selected activator. The most commonly used activating agent is alkylaluminoxane and most preferably methylaluminoxane (MAO) as it promotes high catalytic activity (see for example H. Sinn, W. Kaminsky, H. J. Wollmer, R. Woldt, "Living polymers" with Ziegler catalysts of high productivity. "in Angew. Chem., 92, 396-402, 1980). That activating agent however also exhibits disadvantageous features such as superstoechiometric quantities of MAO ranging from MAO:catalyst precursor ratios of $10^2:1$ to $10^4:1$. Consequently, there is a great need to develop new activating agents that can either replace MAO or decrease its necessary quantities.

The use of borane-based organic Lewis acid as alternative to MAO to activate metallocenes as polymerisation catalysts in homogeneous conditions has been extensively studied by several groups. (see for example: E. Y.-X. Chen, T. J. Marks, "Cocatalysts for metal-catalyzed polymerization: Activators, Activation processes, and structure-activity relationships" in Chem. Rev., 100, 1391-1434, 2000). Preferably the activating agent was a perfluoroborate that comprised a non coordinating anion with a low charge of −1 or −2, that easily achieves charge delocalisation and that is capable of providing single cation active species to a catalyst precursor. It was observed that the catalytic activity was enhanced with the use of perfluoroarylborane in the form of a salt in combination either with trityl $[CPh_3]^{+-}[B(C_6F_5)_4]$ or with ammonium $[HNMe_2Ph]^{+-}[B(C_6F_5)_4]$.

In polymerisation reaction, the cationic moiety of the activating agent reacts with a leaving group of a metal precursor to provide a cationic active site such as for example $(Cp_2$ alkylmetal$)^+$ in the case of metallocene. The latter forms an ion pair with the anionic part of cocatalyst system. The anion weakly coordinates to the metal and is easily exchanged with an olefin monomer, resulting in polymerisation. Unfortunately, these "ion-pair" activating systems suffer from low thermal and chemical stability and are very sensitive to solvents and monomers. The design of stable and robust systems is thus very desirable. In addition, in the case of nitrogen containing cocatalyst compounds, a neutral amine compound is produced during catalyst activation: it can interact strongly with a cationic catalyst, thereby poisoning active sites and competing with olefin monomer coordination. Hence, the polymerisation activity was drastically reduced. To avoid this problem, ammonium cation can be replaced by phosphonium.

Another goal of this invention is the preparation of heterogeneous olefin polymerisation catalytic systems having hardened catalyst grains for use in gas phase or slurry polymerisation processes and then to provide a method for preparing polymers having improved morphology, thereby reducing reactor fouling such as described for example in Fink et al. (G. Fink, B. Steinmetz, J. Zechlin, C. Przybyla, B. Tesche, "Propene polymerization with silica-supported metallocene/MAO catalysts", in Chem. Rev., 100, 1377-90, 2000).

Heterogenisation can optionally be performed by covalent anchorage of the metallocene complexes on mineral oxide supports as described for example in EP-A-293815, or in U.S. Pat. No. 5,262,498, or in U.S. Pat. No. 5,688,880, or in U.S. Pat. No. 5,854,362, or in U.S. Pat. No. 5,399,636 or in H. G. Alt, P. Schertl, A. Koppl, "Polymerization of ethylene with metallocene/methylaluminoxane catalysts supported on polysiloxane microgels and silica." in J. Organometal. Chem., 568, 263-269, 1998, or in M. Galan-Fereres, T. Koch, E. Hey-Hawkins, M. S. Eisen, Moris, "Synthesis and olefin polymerization using supported and non-supported geometry constrained titanium complexes." in J. Organometal. Chem. 580, 145-155, 1999. Similarly, the anchorage of post-metallocene complexes on mineral oxides has been disclosed for example in P. Preishuber-Pflugl, M. Brookhart, "Highly active supported nickel diimine catalysts for polymerization of ethylene" in Macromolecules, 35, 6074-6076, 2002, or in F. A. R. Kaul, G. T. Puchta, H. Schneider, F. Bielert, D. Mihalios, W. A. Herrmann, "Immobilization of bis(imino) pyridyliron(II) complexes on silica." In Organometallics, 74-82, 2002, or in I. Kim, B. H. Han, C.-S. Ha, J.-K. Kim, H. Suh, "Preparation of Silica-Supported Bis(imino)pyridyl Iron(II) and Cobalt(II) Catalysts for Ethylene Polymerization". In Macromolecules, 36, 6689-6691, 2003.

In another strategy, the strong Lewis acid moieties $B(Ar_F)_3$ ($Ar_F$ being perfluorinated aromatic nucleus) were covalently anchored on silica surface by their silanol. Work on the possible anchorage of perfluorinated boranes on different support such as for example polystyrene or silica was reported in U.S. Pat. No. 5,427,991 or in U.S. Pat. No. 5,869,723 or in EP-A-1 359166 or in WO 03/035708. The counter cations of the grafted perfluorinated borate were derivatives of anilinium or trityl cations.

In parallel, Kaneko et al. have anchored the p-trimethoxysilyl-(N,N-dimethylanilinium) on a silica surface to afford an activating support for olefin polymerisation by addition of lithien tetrakis(pentafluorophenyl)borate. They also claim the use of dimethyldimethoxysilane as co-grafting agent.

These catalytic systems using supported activators are less active than equivalent homogeneous systems and the polymer properties are thereby degraded.

There is thus a need to develop new activating supports efficient in producing active single site catalyst systems and that do not require the use of methylaluminoxane as activating agent.

It is an aim of the present invention to prepare new species of activating supports.

It is another aim of the present invention to prepare very active single site supported catalyst systems that do not require the use of methylaluminoxane.

It is also an aim of the present invention to prepare polymers that have regular grain size.

Any one of these aims is at least partially fulfilled by the present invention.

Accordingly, the present invention discloses an activating support for activating metallocene or post-metallocene catalyst components in the homo- or co-polymerisation of ethylene and alpha-olefins characterised in that the activating species is provided either by a pair phosphonium-borate or by a pair phosphonium-aluminate in the presence of a Bronsted acid, said pair being anchored on a silica support.

The present invention also discloses a method for preparing an activating support that comprises the steps of:
a) reacting phosphine $R_3P$ with a borane or an alane in order to provide a classical phosphino-borane or a phosphino-alane pair, wherein each R is independently selected from hydrogen or from substituted or unsubstituted aryl or alkyl having at most 10 carbon atoms, with the restriction that they are not all hydrogen in order to provide steric hindrance, or from $Si(R'O)_{3-n}R''_n$ group wherein R' and R'' are independently selected from alkyl having from 1 to 8 carbon atoms and n is 0, 1, 2 or 3;
b) optionally reacting the reaction product of step a) with a strong Bronsted acid HX wherein X is triflate (OTf) or halogen or $OSi-SiO_2$ or $OS(O_2)-R_F-OSi-SiO_2$, or $OS(O_2)-R_F-Si-SiO_2$, wherein $R_F$ is a perfluorinated alkyl chain;
c) suspending the silica support in an apolar solvent and reacting the complex of step a) or step b) directly with the surface silanol of the silica support;
d) retrieving an activating support.

In a first embodiment according to the present invention, the silanols of the silica support play the role of a Bronsted acid and step b) may thus be omitted. In this scheme, R cannot be $Si(R'O)_{3-n}R''_n$ group. This method of preparation can be represented by Scheme 1.

Scheme 1

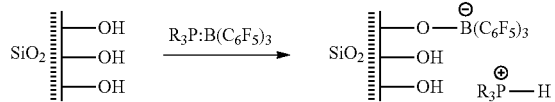

In another embodiment according to the present invention, one R is $Si(R'O)_{3-n}R''_n$ group, said group being preferably used to also anchor the phosphonium part on the silica surface. This method is represented in Scheme 1'.

Scheme 1'

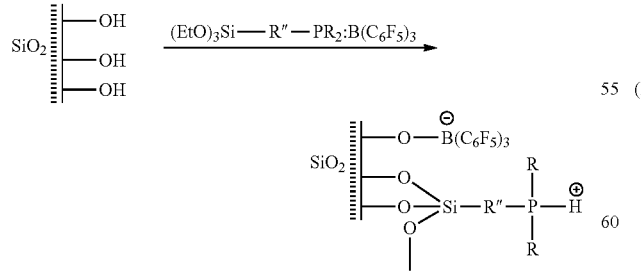

Preferably, the support is silica. Optionally, the support may be modified in order to tailor its acidity, its specific surface, its pore volume, and its hydrophobic or hydrophilic properties. Preferably the supports are modified by addition of aluminium alkyl, preferably $AlMe_3$, to create additional Lewis acid sites or Bronsted acid sites highly suitable for the activation of metallocene components.

Prior to being suspended in the apolar solvent of step c), the silica support may be functionalised with a perfluorinated alkylsulfonic acid chain selected from $SiO_2-OR_F-SO_3H$ or from $SiO_2-R''FSO_3H$ wherein $R_F$ is

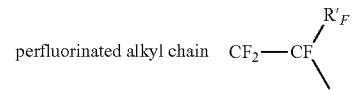

wherein $R'_F$ is $CF_3(CF_2)_n-$ or $(CF_3)_2CF(CF_2)_n-$ and wherein $R''_F$ is $(CH_2)_3-(CF_2)_2O-(CF_2)_2$. Perfluoroalkanesulfonic acid-containing solids, generally called "Nafion" type-functionalised silica, have been previously reported by Harmer et al. in M. A. Harmer, Q. Sun, M. J. Michalczyk, Z. Yang, in *Chem. Commun.*, 1997, 1803-1804; or in D. J. Macquarrie, S. J. Taverner, M. A. Harmer, in *Chem. Commun.*, 2005, 263-265) and by Corma et al. for example in M. Alvaro, A. Corma, D. Das, V. Formes, H. Garcia, in *Chem. Commun.*, 2004, 956-957; or in M. Alvaro, A. Corma, D. Das, V. Fornes, H. Garcia, *J. Catal.*, 2005, 231, 48-55; or in WO 2005051540). That embodiment is represented in scheme 1".

Scheme 1"

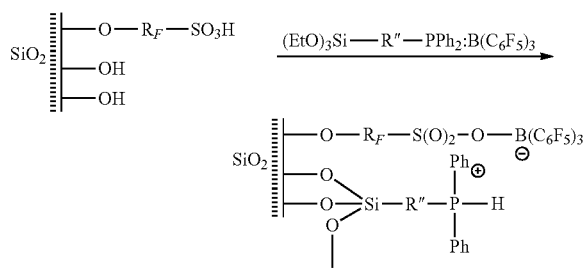

In another embodiment according to the present invention, step b) is present and a strong Bronsted acid HX is added. In this embodiment at least one R is $Si(R'O)_{3-n}R''_n$ group, said group being preferably used to also anchor the phosphonium part on the silica surface. The strong Bronsted acid is additionally used to create a zwitterionic pair phosphonium borate $R_3P^+H$, $X^-BR^1_3$ or phosphonium aluminate $R_3P^+H$, $X^-AlR^1_3$. This is represented in Scheme 2.

Scheme 2

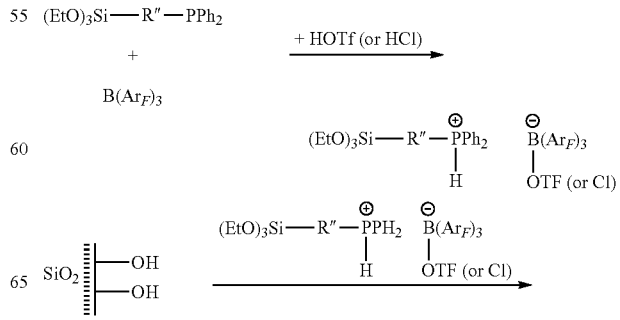

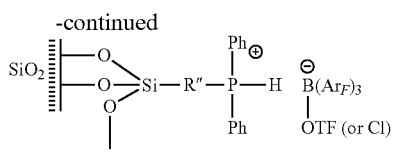

wherein $Ar_F$ is a perfluorinated aryl group.

The activating center may be prepared following the scheme herebelow, prior to being anchored onto the support,

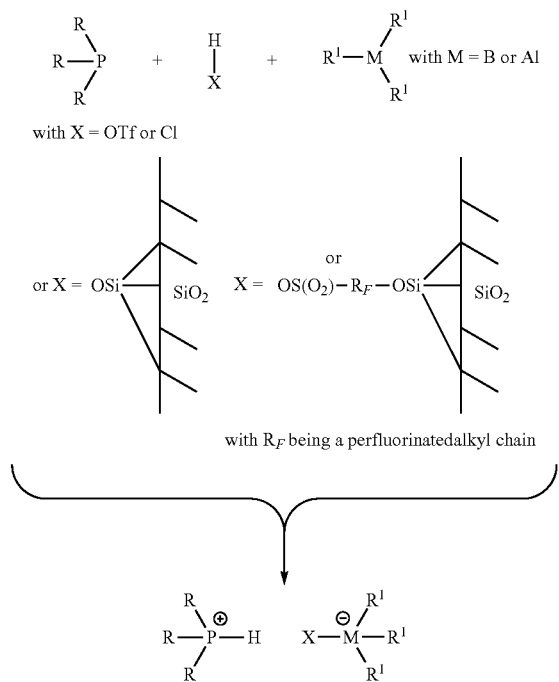

wherein X is triflate (OTf), chlorine, OSi—|—SiO$_2$ or OS(O$_2$)—R$_F$—OSi—|—SiO$_2$, or OS(O$_2$)—R$_F$—Si—|—SiO$_2$, wherein R$_F$ is a perfluorinated alkyl chain and wherein M is B or Al.

The reaction of phosphine P and borane B with ternary system was recently reported by McCahill et al. (J. S. J. McCahill, G. C. Welch, D. W. Stephan in Angew. Chem. Int. Ed. 46, 4968-71, 2007) or in Welch and Stephan (G. C. Welch, D. W. Stephan in J. Am. Chem. Soc. 129, 1880-81, 2007). For instance, the Lewis acid base PB is capable to cleave a H—H bond leading to phosphonium borate (P$^+$H,$^-$BH). Similarly, alkene functions (C=C) are able to activate Lewis acid base PB system allowing the synthesis of phosphonium borate pairs ($^+$P—C—C—B$^-$).

In step a), R$_3$P is preferably reacted with a borane. Among the preferred boranes one can cite B(C$_6$F$_5$)$_3$. Without wishing to be bound by a theory, it is believed that if phosphine is placed directly on the silica it is oxidised. It is protected by complexation with borane without being bound too strongly.

Preferably R are independently selected from hydrogen, methyl, isopropyl, tert-butyl, substituted or unsubstituted phenyl group with the restriction that not all R are hydrogen Si(R'O)$_{3-n}$R''$_n$. Preferably, at least one R is as bulky as or bulkier than isopropyl. In a most preferred embodiment according to the present invention, two R are substituted or unsubstituted phenyl groups and the third R is Si(R'O)$_{3-n}$R''$_n$, providing a chain for anchorage.

The present invention also discloses the double anchorage of zwitterionic system performed by covalently anchoring both the borate or alane anion and the phosphonium cation on a support.

In order to obtain a suitable surface coverage of the silica support by the phosphonium-borate or phosphonium-aluminate pairs, a large excess of the mixture phosphino-borane or phosphino-alane pair must be used. The resulting surface coverage is of from $10^{-3}$ to $5.10^{-3}$ moles of grafts per gram of silica.

Preferably, the support carrying phosphonium complexes is passivated by addition of a non-nucleophile trimethylsilylating agent of formula

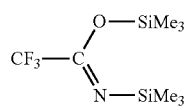

The amount of trimethylsilylating agent is selected to provide at least 5 equivalents of silanol with respect to silanol present in the starting silica-based support.

These new activating supports are suitable for preparing catalyst systems based on single site catalyst components. Metallocene or late transition metal complex catalyst components prepared by any method known in the art can be deposited on the activating supports of the present invention in order to provide active catalyst systems without addition of conventional activating agents such as aluminoxanes or boron-based compounds. Late transition metal complexes of the present invention preferably include α-diimine Ni complexes as disclosed by Brookhart in WO96/23010 or bis(imino)pyridyl Iron(II) or Cobalt(II) complexes as disclosed by Bristovsek et al. (G. J. P. Bristovsek, V. C. Gibson, B. S. Kimberley, P. J. Maddox, S. J. Mc Tavish, G. A. Solan, A. J. P. White, D. J. J. Williams, in Chem. Commun., 849-50, 1998) or in Small et al. (B. L. Small, M. Brookhart, A. M. A. Bennett, in J. Am. Chem. Soc., 120, 4049, 1998).

When the activating supports of the present invention are used with metallocene catalyst components, said components are preferably dialkylated, more preferably dimethylated. Dialkylation can be produced in situ by an alkylating agent such as aluminium alkyl.

The present invention thus discloses a method for oligomerising or for homo- or co-pelimerising ethylene or alpha-olefins that comprises the steps of:

a) providing an activating support as described in any one of the embodiments hereabove;

b) impregnating a dialkylated metallocene or a post-metallocene catalyst component onto the activating support.

c) optionally adding a scavenger;

d) injecting the monomer and optional comonomers simultaneously with or after the catalyst system;

e) maintaining under polymerisation conditions;

f) retrieving an oligomer or a polymer.

The scavenger is typically selected from aluminum alkyl. Preferably it is triethylaluminium (TEAL) or triisobutylaluminium (TIBAL). It is preferable to use a scavenger.

The monomer is preferably ethylene or propylene. The comonomer is preferably ethylene, propylene or 1-hexene.

EXAMPLES

All the reactions are carried out under inert atmosphere, preferably under argon. All the solvents used are anhydrous and distilled Phosphonium/borates or phosphonium/alanes were used to prepare anion-cation pairs.

Preparation of Modified Support S1.

15 g of silica (G5H) from Grace were treated under vacuum at a temperature of 150° C. for a period of time of 24 hours. 40 mL of anhydrous toluene were then added and the suspension was kept under stirring for a period of time of 10 minutes. 10 mL of AlMe$_3$ were then added dropwise. The reaction was exothermal and the solution was kept under stirring at room temperature for a period of time of 1 hour. 300 μL of water were added to the suspension that was kept at room temperature for a period of time of 3 hours. It was then heated at a temperature of 100° C. for a period of time of 16 hours.

$S_{BET}$: 399 m$^2$/g.

$^{27}$Al NMR: 2.46 (six coordinate Al), 54.80 (five coordinate Al).

$^{29}$Si NMR: −57.3, −101.8, −111.1

$^{13}$C NMR: −0.40, 57.56

Elemental analysis: Si$_{mol}$/Al$_{mol}$=15.8

Synthesis of Sample A1:

2.25 g of modified silica/AlMe$_3$ (S1) were activated at a temperature of 150° C. for a period of time of 12 hours. 0.256 g of Ph$_3$P (0.97 mmol) and 0.5 g of B(C$_6$F$_5$)$_3$ (0.97 mmol) were dissolved in 10 mL of toluene. The solution was kept under stirring for a period of time of 30 minutes and then heated at a temperature of 80° C. during 3 hours. The solution was cloudy but it clarified when further heated at a temperature of 80° C. for 6 hours. The solution was added to the activated silica dissolved in 30 mL of toluene to afford a yellow liquid. It was then heated at a temperature of 60° C. for 24 hours. The solid was washed 3 times with 50 mL of toluene and then dried under vacuum for 4 hours.

$S_{BET}$: 315 m$^2$/g

TGA: 0.41 10$^{-3}$ mol/g $^{27}$Al NMR: 2.46 (six coordinate Al), 27.90 (five coordinate Al), 53.52 (five coordinate Al).

$^{29}$Si NMR: −18.5, −100.9, −110.1 ppm $^{13}$C NMR: −0.19, 16.48, 57.41, 128.3, 130.2, 132.5, 133.2, 135.6 ppm $^{11}$B NMR: 34.91 ppm (tetra coordinate B).

$^{31}$P NMR: 30.46 ppm

Elemental analysis: P$_{mol}$/B$_{mol}$=1.4

Synthesis of Sample A2.

2.16 g of Grace silica were activated at a temperature of 150° C. for a period of time of 12 hours. 0.256 g of Ph$_3$P (0.97 mmol) and 0.5 g of B(C$_6$F$_5$)$_3$ (0.97 mmol) were dissolved in 10 mL of toluene. The solution was kept under stirring for a period of time of 30 minutes and then heated at a temperature of 80° C. during 6 hours. The solution was added to the activated silica dissolved in 30 mL of toluene to afford a yellow liquid. It was then heated at a temperature of 60° C. for 24 hours to evaporate the solvent. The solid was washed 3 times with 50 mL of toluene and then dried under vacuum for 4 hours.

S$_{(BET)}$: 145 m$^2$/g

TGA: 0.38 10$^{-3}$ mol/g $^{29}$Si NMR: −100.9 −110.1 ppm $^{13}$C NMR: 128.3, 130.2, 132.5, 133.2, 135.6 ppm $^{11}$B NMR: 26.28 ppm (tetra coordinate B).

$^{31}$P NMR: 32.13 ppm

Elemental analysis: P$_{mol}$/B$_{mol}$=1.3

Synthesis of Sample A3.

1 g of triethoxysilylethyldiphenylphosphine was dissolved in 30 mL of tetrahydrofurane (THE). A stoechiometric amount of B(C$_6$F$_5$)$_3$ (1.39 g) was dissolved in 20 mL of THF and added to the other THF solution. The mixture was kept under stirring for 5 minutes and then trifluoromethane sulfonic acid was added dropwise. The mixture was kept under stirring for 1 hour and heated at a temperature of 60° C. for 12 hours. The solvent was evaporated and the resulting phosphonium borate was dissolved in 20 mL of toluene. 3 g of Grace silica were activated at a temperature of 180° C. for a period of time of 24 hours. It was then suspended in 30 mL of toluene. The solution of phosphonium borate was added dropwise to the support suspension and it was kept under mixing for 1 hour at room temperature (about 25° C.) and then it was heated at a temperature of 80° C. for 12 hours and at a temperature of 100° C. for 3 hours. The toluene was evaporated and the resulting solid was washed several times with toluene. The solid was then dried under vacuum.

$S_{BET}$: 80 m$^2$/g.

TGA: 0.3 10$^{-3}$ mol/g (organic amount).

$^{13}$C NMR: 16.49, 25.75, 28.93, 43.95, 59.47, 68.79, 117.28, 130.16, 133.52. ppm $^{11}$B NMR: 24.57 ppm (tetra coordinate B).

$^{31}$P NMR: 14.95 ppm

Synthesis of Sample A4:

This sample was prepared by reacting triethoxyethyldiphenylphosphine, borane and an heterogeneous support (S2) (1,2,2-trifluoro-1-trifluoromethyl-ethane sulfonic acid-containing silica gel).

a) Preparation of Support S2:

1,2,2-trifluoro-1-trifluoromethyl-ethane sulfonic acid-containing silica gel was prepared according the procedure described in M. Alvaro, A. Corma, D. Das, V. Formes, H. Garcia, *J. Catal.*, 2005, 231, 48-55; or in WO 2005051540: A solution of 0.8 g (3.5 mmol) of 1,2,2-trifluoro-2-hydroxyl1-(trifluoromethyl)-ethane sulfonic acid beta-sultone (from ABCR chemicals) in dry toluene (20 mL) was added at room temperature to a suspension of 4 g of cooled activated silica gel ((G5H) (treated under vacuum at a temperature 150° C. during 8 h) in toluene (25 mL) under argon. After stirring at room temperature during 30 min, the reaction mixture was heated at a temperature of 80° C. during 12 h then at a temperature of 100° C. during 3 h more. After cooling, the solid was filtered and washed under argon with dry toluene (30 mL, 2 times), then with pentane (20 mL) then evacuated under vacuum 4 h. The perfluorosulfonic acid loading determined by thermogravimetry is 0.54 mmol.g$^{-1}$.

b) Reaction of Phosphino Borane with Support (S2):

the obtained support S2 was activated under vacuum at 80° C. for 6 hours. Then, 30 mL of distilled toluene were added. The solution was stirred for 30 nm. A solution of triethoxysilylethyldiphenylphosphine (0.18 g, 0.7 10$^{-3}$ mol), B(C$_6$F$_5$)$_3$ (0.20 g, 0.7 10$^{-3}$ mol) and 20 mL of toluene was heated for 2 hours. The phosphino-borane solution was added to the solution of S2 in toluene. The mixture was stirred at room temperature for 1 hour and then, heated at 100° C. for 12 h. After separation by filtration under argon, the solid was washed five times under argon with toluene (30 mL). The solid was then dried under vacuum for 6 hours.

In sample A4, only the cationic part was anchored on the silica support and the anionic part was free. In sample A'4, both cationic and anionic parts were anchored on the support.

$S_{BET}$: 148 m$^2$/g.

TGA: 0.25 mmol/g.

Elemental Analysis: P$_{mol}$/B$_{mol}$=1.6

Polymerisation of Ethylene:

The activating supports prepared in the examples hereabove were used in the polymerisation of ethylene under the following conditions:

Solvent: 20 mL of heptane
Scavenger: 1 mL of triisobutylaluminium (TIBAL)
Pressure: 15 bars of ethylene
Temperature: 50° C.
Polymerisation time: 30 minutes
Stirring was carried out at 1000 rpm
Metallocene catalyst component: a fresh solution of the dimethylated catalyst system sold by Total Petrochemicals under the name Z12Hsm.
Activating support: 10 mg of activating support.

The polymerisation conditions and results are reported in Table I.

TABLE I

| Activator | Molar ratio metal/activator | Productivity g/g/h | Activity kg/mmol/h |
|---|---|---|---|
| A1 | 2.29 | 452 | 2.48 |
| A2 | 2.10 | 183 | 1.0 |
| A3 | 1.15 | 241 | 0.91 |
| A4 | 1.12 | 349 | 2.66 |
| A'4 | 1.15 | 269 | 1.23 |

The invention claimed is:

1. A method for preparing an activating support comprising:
    a) reacting phosphine $R_3P$ with a borane or an alane, wherein each R is independently selected from hydrogen, a substituted or unsubstituted aryl or alkyl having at most 10 carbon atoms, or an $Si(R'O)_{3-n}R''_n$ wherein R' and R'' are independently selected from alkyl having from 1 to 8 carbon atoms and n is 0, 1, 2 or 3, wherein not all Rs are hydrogen;
    b) optionally reacting the reaction product of step a) with a strong Bronsted acid HX wherein X is triflate (OTf) or halogen or OSi—|—$SiO_2$ or $OS(O_2)$—$R_F$—OSi—|—$SiO_2$, or $OS(O_2)$—$R_F$—Si—|—$SiO_2$, whererin $R_F$ is a perfluorinated alkyl chain;
    c) suspending the silica support in an apolar solvent and reacting the complex of step a) or step b) directly with the surface silanol of the silica support; and
    d) retrieving an activating support.

2. The method of claim 1, wherein step b) is omitted.

3. The method of claim 1, wherein step b) is present and at least one R is $Si(R'O)_{3-n}R''_n$ group.

4. The method of claim 1, wherein the silica support is functionalised with a perfluorinated alkyl chain selected from the group consisting of $SiO_2$—$OR_F SO_3H$ and $SiO_2$—$R''_f SO_3H$ wherein

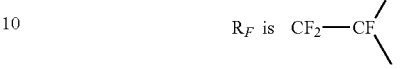

wherein $R'_F$ is $CF_3(CF_2)_n$— or $(CF_3)_2CF(CF_2)_n$— and wherein $R''_f$ is $(CH_2)_3$—$(CF_2)_2$—O—$(CF_2)_2$.

5. The method of claim 1, wherein a borane is used in step a).

6. The method of claim 1, wherein X is OTf.

7. The method of claim 1, wherein the support is a silica support modified by addition of an aluminium aluminum alkyl.

8. The method of claim 1, wherein the activating support is contacted by a non-nucleophile trimethylsilylating agent.

9. An activating support obtained by claim 1 wherein the activating species is a pair phosphonium-borate or a pair phosphonium-aluminate in the presence of a Bronsted acid, said pair anchored on a silica support.

10. A method for oligomerising or homo- or co-polymerising ethylene and alpha-olefins that comprises the steps of:
    a) providing the activating support of claim 9;
    b) impregnating a dialkylated metallocene onto the activating support;
    c) injecting the monomer and optional comonomer simultaneously with or after the catalyst system;
    d) optionally injecting a scavenger;
    e) maintaining under polymerisation conditions; and
    f) retrieving a polymer or an oligomer.

11. The method of claim 10, wherein the monomer is ethylene or propylene and the comonomer is ethylene, propylene or 1-hexene.

* * * * *